US012213813B2

(12) United States Patent
Chamorro et al.

(10) Patent No.: US 12,213,813 B2
(45) Date of Patent: Feb. 4, 2025

(54) MOBILE SURGICAL CONTROL CONSOLE

(71) Applicant: Covidien LP, Mansfield, MA (US)

(72) Inventors: Andres Chamorro, Boston, MA (US); Cameron Cecil, Boston, MA (US); William Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 1271 days.

(21) Appl. No.: 16/645,333

(22) PCT Filed: Sep. 5, 2018

(86) PCT No.: PCT/US2018/049454
§ 371 (c)(1),
(2) Date: Mar. 6, 2020

(87) PCT Pub. No.: WO2019/050883
PCT Pub. Date: Mar. 14, 2019

(65) Prior Publication Data
US 2021/0022821 A1    Jan. 28, 2021

Related U.S. Application Data

(60) Provisional application No. 62/554,638, filed on Sep. 6, 2017.

(51) Int. Cl.
*A61B 50/13*    (2016.01)
*A61B 34/30*    (2016.01)
(Continued)

(52) U.S. Cl.
CPC .............. *A61B 50/13* (2016.02); *A61B 34/30* (2016.02); *A61B 50/10* (2016.02); *B25J 5/007* (2013.01);
(Continued)

(58) Field of Classification Search
CPC .................... A61B 50/10; A61B 50/13; A61B 2017/00199; B25J 5/007; B62B 1/12; B62B 1/125; B62B 3/02
See application file for complete search history.

(56) References Cited

U.S. PATENT DOCUMENTS 6,246,200 B1 * 6/2001 Blumenkranz ........ A61B 34/70
                                                            318/568.25
6,629,927 B1   10/2003 Mesaros et al.
(Continued)

FOREIGN PATENT DOCUMENTS

JP    2002017784 A    1/2002
JP    2004514464 A    5/2004
(Continued)

OTHER PUBLICATIONS

Chinese First Office Action dated Sep. 20, 2022 corresponding to counterpart Patent Application CN 201880006217.
(Continued)

*Primary Examiner* — Jeffrey J Restifo
(74) *Attorney, Agent, or Firm* — Carter, DeLuca & Farrell LLP

(57) ABSTRACT

A mobile surgical control console is provided and includes a base housing, a lower frame assembly, a plurality of vertical supports, a monitor, and an upper frame assembly. The lower frame assembly further includes a proximal end, a distal end and an opening defined therethrough which extends through the proximal end thereof. The lower frame assembly is coupled to the base housing. The plurality of vertical supports each have an inferior end and a superior end, and each vertical support is attached to the base housing. The monitor is attached to the superior end of each vertical support. The upper frame assembly includes an upper frame and a mobile section. The upper frame includes a proximal end, a distal end and an opening defined there-
(Continued)

through. The upper frame is supported on each vertical support. The mobile section is supported by the upper frame.

9 Claims, 15 Drawing Sheets

(51) Int. Cl.
*A61B 50/10* (2016.01)
*B25J 5/00* (2006.01)
*B25J 9/00* (2006.01)
*A61B 17/00* (2006.01)

(52) U.S. Cl.
CPC ... *B25J 9/0009* (2013.01); *A61B 2017/00199* (2013.01)

(56) References Cited

U.S. PATENT DOCUMENTS

| | | | |
|---|---|---|---|
| 7,533,892 B2* | 5/2009 | Schena | B62D 7/09 |
| | | | 280/47.11 |
| 8,828,023 B2 | 9/2014 | Neff et al. | |
| 9,308,937 B2* | 4/2016 | Griffiths | A61B 50/10 |
| 10,231,792 B2* | 3/2019 | Shiels | A61B 34/30 |
| 10,893,912 B2* | 1/2021 | Crawford | A61B 34/30 |
| 10,898,252 B2* | 1/2021 | Johnson | A61B 17/7011 |
| 10,925,681 B2* | 2/2021 | Johnson | B25J 9/1633 |
| 10,973,594 B2* | 4/2021 | Crawford | A61B 34/25 |
| 11,097,758 B1* | 8/2021 | Lee | A63F 13/90 |
| 11,207,150 B2* | 12/2021 | Healy | A61B 90/37 |
| 11,504,462 B2* | 11/2022 | Hyde | A61M 60/00 |
| 11,850,009 B2* | 12/2023 | Crawford | A61B 17/3421 |
| 11,857,273 B2* | 1/2024 | Crawford | A61B 34/30 |
| 11,864,857 B2* | 1/2024 | Chappuis | A61B 34/37 |
| 12,053,309 B2* | 8/2024 | Liang | F16L 27/0804 |
| 12,064,196 B2* | 8/2024 | Lee | A61B 34/37 |
| 2005/0275178 A1* | 12/2005 | Huesdash | F16M 11/42 |
| | | | 280/47.35 |
| 2005/0288571 A1 | 12/2005 | Perkins et al. | |
| 2006/0039105 A1 | 2/2006 | Smith et al. | |
| 2007/0043338 A1* | 2/2007 | Moll | A61B 34/30 |
| | | | 606/1 |
| 2008/0252045 A1* | 10/2008 | Rossini | B62B 3/02 |
| | | | 280/659 |
| 2011/0025007 A1* | 2/2011 | Butler | A61G 12/001 |
| | | | 280/47.35 |
| 2011/0232535 A1* | 9/2011 | Hung | A61G 12/001 |
| | | | 108/50.02 |
| 2012/0212116 A1* | 8/2012 | McRorie | A61B 50/13 |
| | | | 312/249.13 |
| 2014/0005679 A1* | 1/2014 | Shelton, IV | A61B 17/072 |
| | | | 606/130 |
| 2014/0035262 A1 | 2/2014 | White et al. | |
| 2014/0243849 A1 | 8/2014 | Saglam et al. | |
| 2014/0265193 A1* | 9/2014 | Stark | F16M 11/045 |
| | | | 248/289.11 |
| 2015/0025549 A1 | 1/2015 | Kilroy et al. | |
| 2015/0166090 A1* | 6/2015 | Hardy | A61B 50/15 |
| | | | 280/47.35 |
| 2015/0196192 A1* | 7/2015 | Kan | F16M 11/42 |
| | | | 211/85.13 |
| 2015/0223890 A1* | 8/2015 | Miller | A61B 50/10 |
| | | | 726/17 |
| 2016/0006992 A1* | 1/2016 | Roberts | H04N 23/63 |
| | | | 348/113 |
| 2016/0367329 A1 | 12/2016 | Dekel | |
| 2017/0172674 A1 | 6/2017 | Hanuschik et al. | |
| 2017/0316705 A1* | 11/2017 | Schultz | G16H 30/20 |
| 2018/0256427 A1 | 9/2018 | Volek et al. | |
| 2018/0296299 A1* | 10/2018 | Iceman | A61B 34/30 |
| 2018/0311005 A1 | 11/2018 | Mccormick et al. | |
| 2018/0360553 A1 | 12/2018 | Nakanishi | |
| 2019/0059859 A1* | 2/2019 | Pinch | A61B 8/4433 |
| 2020/0206946 A1* | 7/2020 | Bondaryk | B66F 9/20 |
| 2020/0290660 A1* | 9/2020 | Wright | A61B 50/13 |
| 2021/0012917 A1* | 1/2021 | Nunn | G01T 7/00 |
| 2021/0022821 A1* | 1/2021 | Chamorro | A61B 34/30 |
| 2021/0068532 A1* | 3/2021 | Blewett | A47B 9/20 |
| 2021/0070338 A1* | 3/2021 | Wright | A61B 50/13 |
| 2022/0226180 A1* | 7/2022 | Lawson | A61B 50/13 |
| 2023/0102735 A1* | 3/2023 | Qian | G02B 27/017 |
| | | | 606/1 |
| 2023/0182303 A1* | 6/2023 | Wells | A61B 34/30 |
| | | | 700/250 |
| 2023/0200922 A1* | 6/2023 | Huang | A61B 34/30 |
| 2023/0277256 A1* | 9/2023 | Soto | A61B 34/20 |
| | | | 700/245 |
| 2023/0285089 A1* | 9/2023 | Manfrin | A61B 34/25 |
| 2023/0285090 A1* | 9/2023 | Lee | A61B 34/37 |
| 2023/0285093 A1* | 9/2023 | Crawford | B25J 9/1065 |
| 2023/0285614 A1* | 9/2023 | Kotani | A61B 50/33 |
| 2023/0346489 A1* | 11/2023 | Naclerio | B25J 5/007 |
| 2023/0355456 A1* | 11/2023 | Schmitt | A61G 13/0018 |

FOREIGN PATENT DOCUMENTS

| | | |
|---|---|---|
| JP | 2006519684 A | 8/2006 |
| JP | 2009500086 A | 1/2009 |
| JP | 2013017708 A | 1/2013 |
| JP | 2016520334 A | 7/2016 |
| WO | 2010021447 A1 | 2/2010 |

OTHER PUBLICATIONS

Japanese Office Action mailed Jun. 15, 2022 corresponding to counterpart Patent Application JP 2020-513292.
Extended European Search Report dated Jun. 3, 2021 corresponding to counterpart Patent Application EP 18854193.2.
Indian Office Action dated Apr. 25, 2022 corresponding to counterpart Patent Application IN 202017009814.
European Office Action dated Jun. 2, 2022 corresponding to counterpart Patent Application EP 18 854 193.2.
International Search Report mailed Dec. 20, 2018 and Written Opinion completed Dec. 20, 2018 corresponding to counterpart Int'l Patent Application PCT/US2018/049454.

* cited by examiner

MOBILE SURGICAL CONTROL CONSOLE

CROSS-REFERENCE TO RELATED APPLICATIONS

This application is a U.S. National Stage Application filed under 35 U.S.C. § 371(a) of International Patent Application Serial No. PCT/US2018/049454, filed Sep. 5, 2018, which claims the benefit of and priority to U.S. Provisional Patent Application Ser. No. 62/554,638, filed Sep. 6, 2017, the entire disclosure of which is incorporated by reference herein.

BACKGROUND

Robotic surgical systems have been used in minimally invasive medical procedures. Some robotic surgical systems include a surgical robotic console supporting a surgical robotic arm and a surgical instrument, having at least one end effector (e.g., forceps, or a grasping tool), mounted to the robotic arm. The robotic arm provides mechanical power to the surgical instrument for its operation and movement. Each robotic arm may include an instrument drive unit that is operatively connected to the surgical instrument. Additionally, robotic surgical systems include surgical control consoles including a base, a visual assembly and controls to manipulate the surgical robotic arms of the surgical robotic console, that provide mechanical power to the surgical instrument for its operation and movement.

Typically, robotic surgical systems are used within medical settings, such as a hospital. In accordance with industry standards and codes, most hospitals are constructed to include threshold, such as doorways, with a fixed width of about 33 inches. However, robotic surgical systems, specifically the surgical control console components, are design to include a fixed width greater than about 33 inches. Additionally, a surgical control console is also commonly configured to be stationary and positioned in one designated medical room. Both of these design aspects of majority of robotic surgical systems, specifically surgical control console components, limits mobility of the surgical control console and a compatibility of the surgical control console with multiple surgical systems.

Accordingly, a need exists for a surgical control console having mobility or at least improved mobility.

SUMMARY

The present disclosure relates to a mobile surgical control console and methods for moving the mobile surgical control console.

According to an aspect of the present disclosure, a mobile surgical control console is provided and includes a base housing, a lower frame assembly, a plurality of vertical supports, a visual assembly, and an upper frame assembly. The lower frame assembly further includes a proximal end, a distal end, and an opening defined therethrough and which extends through the proximal end thereof. A plurality of wheels is attached to the lower frame assembly and the lower frame assembly is coupled to the base housing. The plurality of vertical supports each have an inferior end and a superior end, and each vertical support is attached to the base housing. The visual assembly is attached to the superior end of each vertical support. The upper frame assembly includes an upper frame and a mobile section. The upper frame includes a proximal end, a distal end and an opening defined therethrough. The upper frame is supported on each vertical support. The mobile section is supported by the upper frame. The mobile surgical console includes a first dimension and a second dimension, wherein the first dimension, the mobile surgical console has a width greater than 33 inches and a length greater than 44 inches, and in the second dimension, the mobile surgical console has a width and a length.

In another aspect of the present disclosure, the mobile section may be displaced from the upper frame. In some embodiments, the mobile section is configured to be detached from the upper frame. In other embodiments, the mobile section is pivotably coupled to the upper frame, wherein the mobile section pivots between a first position and a second position. In yet other embodiments, the mobile section includes a first end and a second end that are each configured to fit within a track portion included within the upper frame. The mobile section is configured to translate from a first position within the track portion and a second position within the track portion.

The mobile section may be positioned within the proximal end of the upper frame and the lower frame assembly may be substantially U-shaped. In some embodiments, the opening in the lower frame assembly is axially aligned with the mobile section of the upper frame assembly.

The lower frame assembly may include at least one hinged section allowing the lower frame assembly to transition from a first position and a second position. The lower frame assembly may also include a locking mechanism for locking the lower frame assembly in the first position and the second position.

In another aspect of the present disclosure, the mobile surgical console includes a base housing, a lower frame assembly, a plurality of vertical supports, a visual assembly and an upper frame. The lower frame assembly further includes a proximal end, a distal end, and an opening defined therethrough and which extends through the proximal end thereof. A plurality of wheels is attached to the lower frame assembly and the lower frame assembly is coupled to the base housing. The plurality of vertical supports each have an inferior end and a superior end, and each vertical support is attached to the base housing. The visual assembly is attached to the superior end of each vertical support. The upper frame includes a proximal end, a distal end, and an opening defined therethrough. The upper frame is supported on each vertical support. The upper frame may be displaced. In one embodiment, the upper frame is completely removable from the plurality of vertical supports. In another embodiment, the upper frame pivots between a first position and a second position. Also in this embodiment, the upper frame includes a locking mechanism for locking the upper frame in the first position and in the second position. The lower frame assembly further includes at least one hinged section allowing the lower frame assembly to transition from a first position and a second position and a locking mechanism for locking the lower frame assembly in the first position and in the second position.

In a method for moving a mobile surgical console of the present disclosure, the lower frame is transitioned from a first position to a second position, the mobile section is removed from the upper frame to define an upper frame opening which is aligned with the opening of the lower frame assembly. The mobile surgical console is then moved across a threshold from a first location to a second location, wherein the mobile surgical console is pivoted through the threshold by first receiving a portion of the threshold into the opening of the lower frame assembly and the opening of the upper frame assembly.

BRIEF DESCRIPTION OF DRAWINGS

Various aspects and features of the present disclosure are described hereinbelow with reference to the drawings, wherein.

DETAILED DESCRIPTION

As used herein, the term "clinician" refers to a doctor, nurse, or other care provider and may include support personal. As used herein, the term "distal" refers to that portion of the mobile surgical control console, the robotic surgical system, or components thereof, that is farther from a clinician, while the term "proximal" refers to that portion of the mobile surgical control console, the robotic surgical system, or components thereof, that is closer to the clinician. Additionally, as used herein, the terms superior, inferior, anterior, and interior are used to describe portion of the mobile surgical control console, robotic surgical system, or components thereof, with the general understanding of the terms. In the following description, well-known functions or constructions are not described in detail to avoid obscuring the present disclosure in unnecessary detail.

As will be described in detailed below, provided is a mobile surgical control console configured to connect with a robotic surgical system. As will be disclosed in greater detailed below, mobile surgical control console includes a lower frame assembly, a base housing, vertical supports, and an upper frame assembly.

Figure 1:
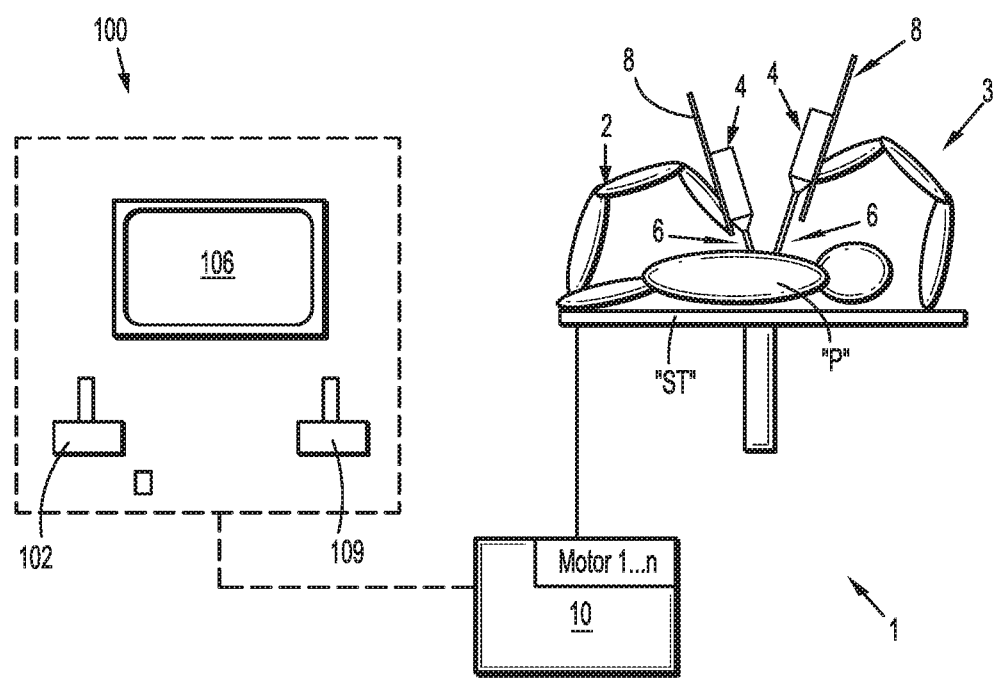
FIG. 1 is a schematic view of a robotic surgical system and a mobile surgical control console of the present disclosure.

Referring initially to FIG. 1, a surgical system, such as, for example, a robotic surgical system 1, generally includes one or more surgical robotic arms 2, 3, a control device 10, and an operating console, such as, for example, a mobile surgical control console 100 coupled with control device 10. Any of the surgical robotic arms 2, 3 may have a robotic surgical assembly 4 and an electromechanical surgical instrument 6 coupled thereto. In some embodiments, the robotic surgical assembly 4 may be removably attached to a slide rail 8 of one of the surgical robotic arms 2, 3. In certain embodiments, the robotic surgical assembly 4 may be fixedly attached to the side rail 8 of one of the surgical robotic arms 2, 3.

Mobile surgical control console 100, which will be described in further detailed below, includes a display device, such as, for example, a monitor 106 set up to display three-dimensional images; and manual input devices 102, 104, by means of which a clinician (not shown), is able to telemanipulate the robotic arms 2, 3 in a first operating mode, as known in principle to a person skilled in the art. Each of the robotic arms 2, 3 may be composed of any number of members, which may be connected through joints. The robotic arms 2, 3 may be driven by electric drives (not shown) that are connected to control device 10. The control device 10 (e.g., a computer) is set up to activate the drives, for example, by means of a computer program, in such a way that the robotic arms 2, 3, the attached robotic surgical assembly 4, and thus the electromechanical surgical instrument 6 (including the electromechanical end effector, not shown) execute a desired movement according to a movement defined by means of the manual input devices 102, 104. The control device 10 may also be set up in such a way that it regulates the movement of the robotic arms 2, 3, and/or of the drives.

The robotic surgical system 1 is configured for use on a patient "P" positioned (e.g., lying) on a surgical table "ST" to be treated in a minimally invasive manner by means of a surgical instrument, e.g., the electromechanical surgical instrument 6. The robotic surgical system 1 may also include more than two robotic arms 2, 3, the additional robotic arms likewise connected to the control device 10 and telemanipulatable by means of the mobile surgical control console 100. A surgical instrument, for example, the electromechanical surgical instrument 6 (including the electromechanical end effector thereof), may also be attached to any additional robotic arm(s).

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2:
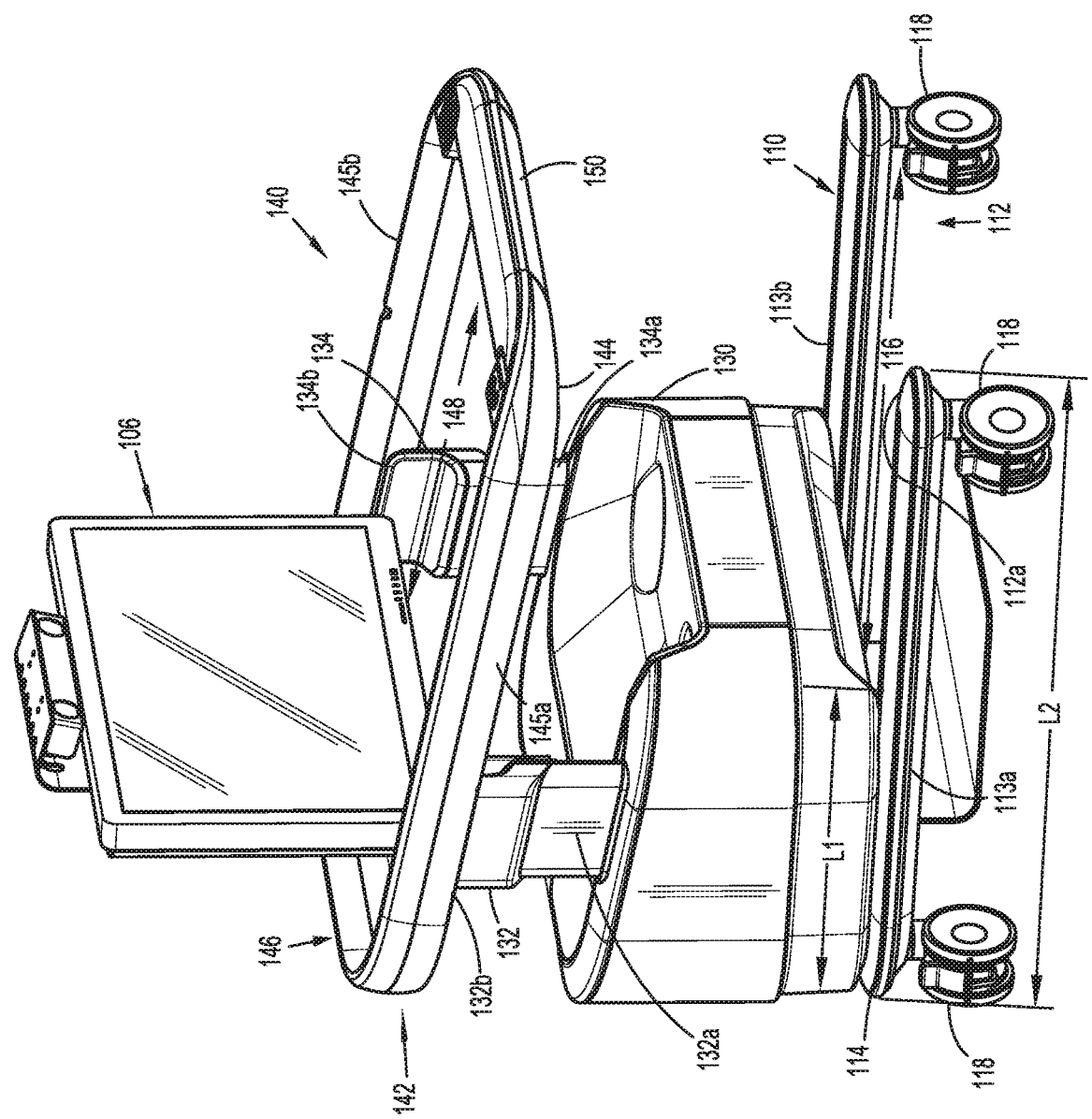
FIG. 2 is a perspective view of the mobile surgical control console in accordance with the present disclosure.

Turning now to FIG. 2, the mobile surgical control console 100, according to the present disclosure, includes a lower frame assembly 110, a base housing 130, vertical supports 132, 134, a monitor 106, and an upper frame assembly 140. The lower frame assembly 110 includes a proximal end 112, a distal end 114, and an opening 116. In one embodiment, the configuration of the proximal end 112, the distal end 114, and the opening 116 may resemble a U-shaped frame. In this embodiment the proximal end 112 and the distal end 114 are connected via a pair of evenly spaced apart beams or legs 113a, 113b. The proximal end 112 and the distal end 114 may be unitarily formed with beams 113a, 113b. Also, in embodiments, where the lower frame assembly 110 is a U-shaped frame, the opening 116, defined between the distal end 114 and the proximal end 112, extends through the proximal end 112. In other embodiments, the configuration of the proximal end 112, the distal end 114, and the opening 116 may form a square shaped frame, rectangular shaped frame or any other suitable shape.

Turning momentarily to FIGS. 10-13, in an embodiment of the present disclosure, each beam 113a, 113b of the lower frame assembly 110 may include a hinged section 120a, 120b, respectively. Hinged sections 120a, 120b may be located anywhere along beams 113a, 113b. Also, hinged sections 120a, 120b may allow a swinging motion and/or a pivoting motion as discussed in further detail below. As illustrated in FIG. 2, lower frame assembly 110 includes wheels 118 attached to an inferior surface thereof. At least two wheels 118 may be attached to each beam 113a, 113b of the lower frame assembly 110. Also, wheels 118 may be attached anywhere upon the inferior surface of lower frame assembly 110.

Referring back to FIG. 2, the base housing 130 may have a general shape of a cube, rectangle, cylinder or any other appropriate shape. Also, the base housing 130 has a proximal side, a distal side, a superior portion and an inferior portion. The base housing 130 may be hollow or semi-hollow. Due to the hollow or semi-hollow characteristic of base housing 130, the base housing 130 may house other components, such as electrical wires (not shown), a mobile power source (not shown) or any other appropriate component.

The base housing 130 may also include grooves or apertures on the superior portion that are compatible with the vertical supports 132, 134. Each vertical support 132, 134 has an inferior end 132a, 134a and a superior end 132b, 134b, respectively. Also, each vertical support 132, 134 has an anterior surface and an exterior surface. Each superior end 132b, 134b of respective vertical supports 132, 134 may include a grove or channel located in the anterior surface, thereof. The shape of vertical supports 132, 134 may be rectangular, cylinder or any other appropriate shape.

The upper frame assembly 140 includes an upper frame 142 and a mobile section 150. The upper frame 142 includes a proximal end 144, a distal end 146, and an opening 148. The proximal end 144 and the distal end 146 are connected via beams or arms 145a, 145b. The mobile section 150 may be removably located in the proximal end 144 of the upper frame 142.

With continue reference to FIG. 2, one configuration of the mobile surgical control console 100 will be described. The inferior portion of the base housing 130 is configured to rest upon or otherwise connected to the lower frame assembly 110. The distal side of base housing 130 aligns with the distal end 114 of the lower frame assembly 110. In some embodiments, a length "L1" of base housing 130 is approximately one-half of a length "L2" of the lower frame assembly 110.

The vertical supports 132, 134 connect the monitor 106 and the upper frame assembly 140 to the base housing 130. Alternatively, as illustrated in FIGS. 5, and 9-12, monitor 106 may be supported on a superior end of a monitor vertical support 232 which extends from the base housing 130. Inferior ends 132a, 134a of vertical supports 132, 134 are fitted within the grooves or apertures located on the superior portion of the base housing 130. Also, it is contemplated that the grooves or apertures of the base housing 130 are spaced evenly apart from one another and are located adjacent to the outer perimeter of the superior portion of the base housing 130; however, the grooves or apertures may be located anywhere on the superior portion of the base housing 130. Superior ends 132b, 134b of vertical supports 132, 134 are configured to support the monitor 106, as well as connect the upper frame assembly 140 to the base housing 130. While, monitor 106 is sized to fit in between superior ends 132b, 134b, it is contemplated that any size monitor 106 may be provided and supported on superior ends 132b, 134b of vertical supports 132, 134.

The upper frame assembly 140 is dimensioned to extend around superior ends 132b, 134b of the vertical supports 132, 134, with the superior ends 132b, 134b connecting to an interior surface of the upper frame assembly 140. The vertical supports 132, 134 may include an adjustment mechanism, whereby a clinician may adjust the height of the mobile surgical control console 100 by adjusting the length of the vertical supports 132, 134. In an embodiment, the lower frame assembly 110 and the upper frame assembly 140 are arranged substantially parallel to one another.

In accordance with the present disclosure, the lower frame assembly 110 and the upper frame assembly 140 align with one another so that the opening 116 defined through the proximal end 112 of the lower frame assembly 110 aligns with the mobile section 150 of the upper frame assembly 140. Similarly, beams 113a, 113b of lower frame assembly 110 may be located substantially in a common plane as 145a, 145b of upper frame assembly 140, so as to overlie one another.

The dimension of each of the lower frame assembly 110, base housing 130, vertical supports 132, 134 and upper frame assembly 140 will be discussed in detail below. Also, the dimension of the entire mobile surgical control console 100 will be discussed in detail below.

Figure 3:
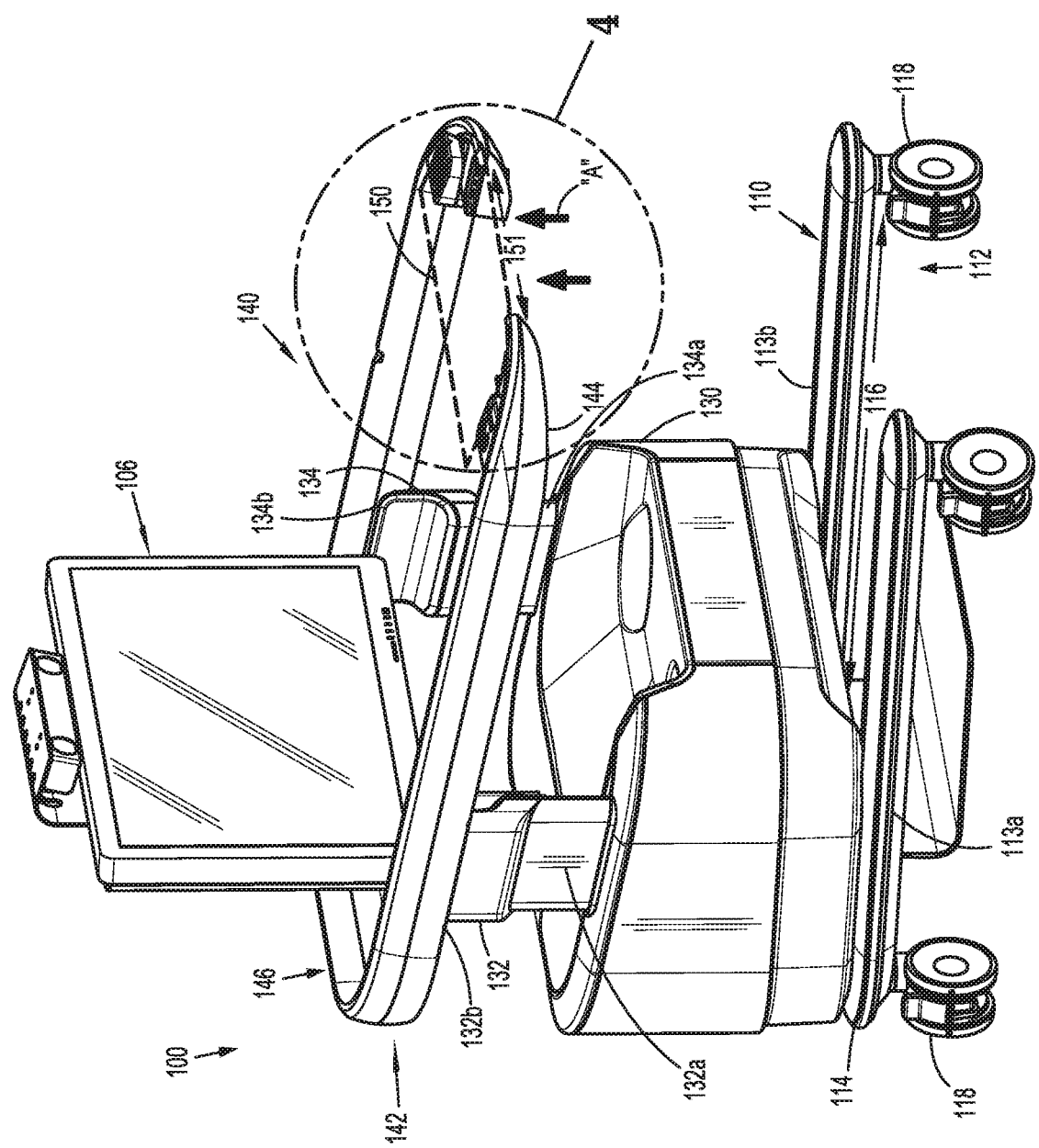
FIG. 3 is a perspective view of the mobile surgical control console of FIG. 2 with a mobile section removed therefrom.
Figure 4:
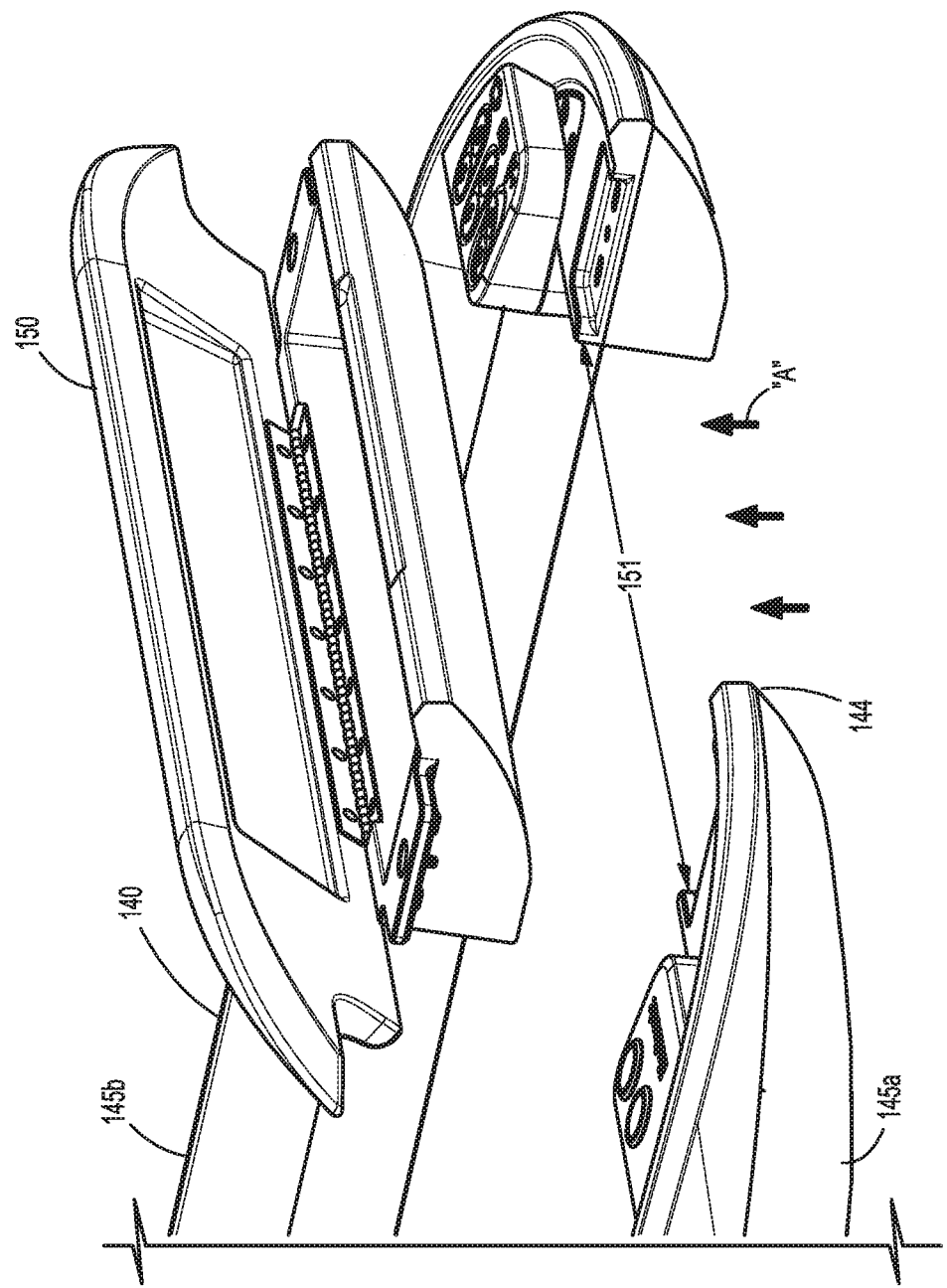
FIG. 4 is an enlarged perspective view of the mobile section of FIG. 3, shown removed from the mobile surgical control console.
Figure 5:
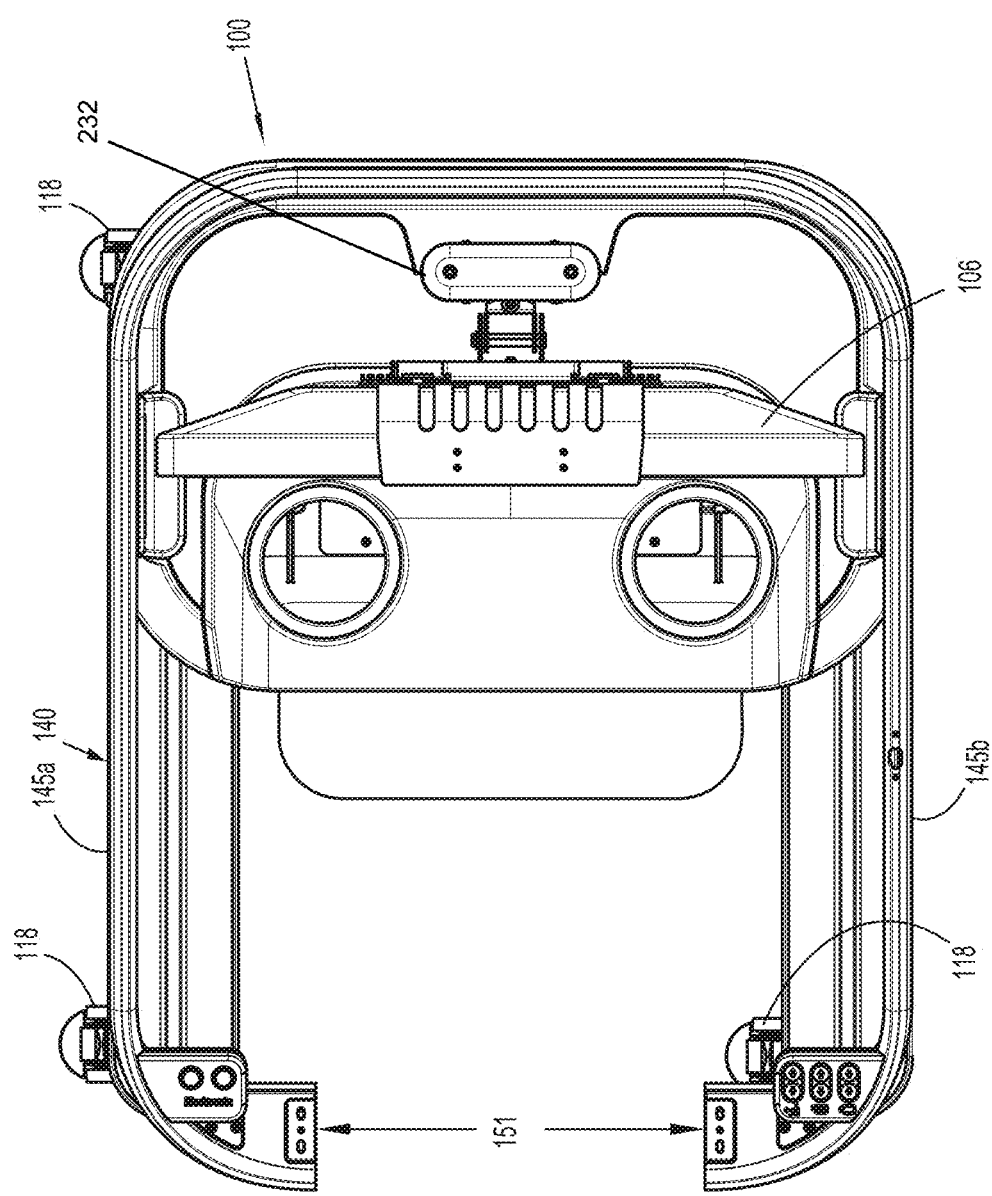
FIG. 5 is a top plan view of the mobile surgical control console of FIG. 2 with the mobile section removed therefrom.

As illustrated in FIGS. 3, 4, and 5, the mobile section 150 is removably connected to the upper frame assembly 140. In one embodiment, mobile section 150 is completely detachable from the upper frame assembly 140. In this embodiment, mobile section 150 may be connected to the upper frame assembly 140 via a snap-fitting, which allows a clinician to snap the mobile section 150 in and out of the upper frame assembly 140. A clinician may detach the mobile section 150 by exerting upward force upon the mobile section 150 (e.g., upward force illustrated by arrows A). Once the mobile section 150 is removed from the upper frame assembly 140, an aperture or opening 151 is created within the upper frame assembly 140. This aperture or opening 151 is axially aligned with or in registration with the opening 116 defined through the proximal end 112 of the lower frame assembly 110.

Figure 6:
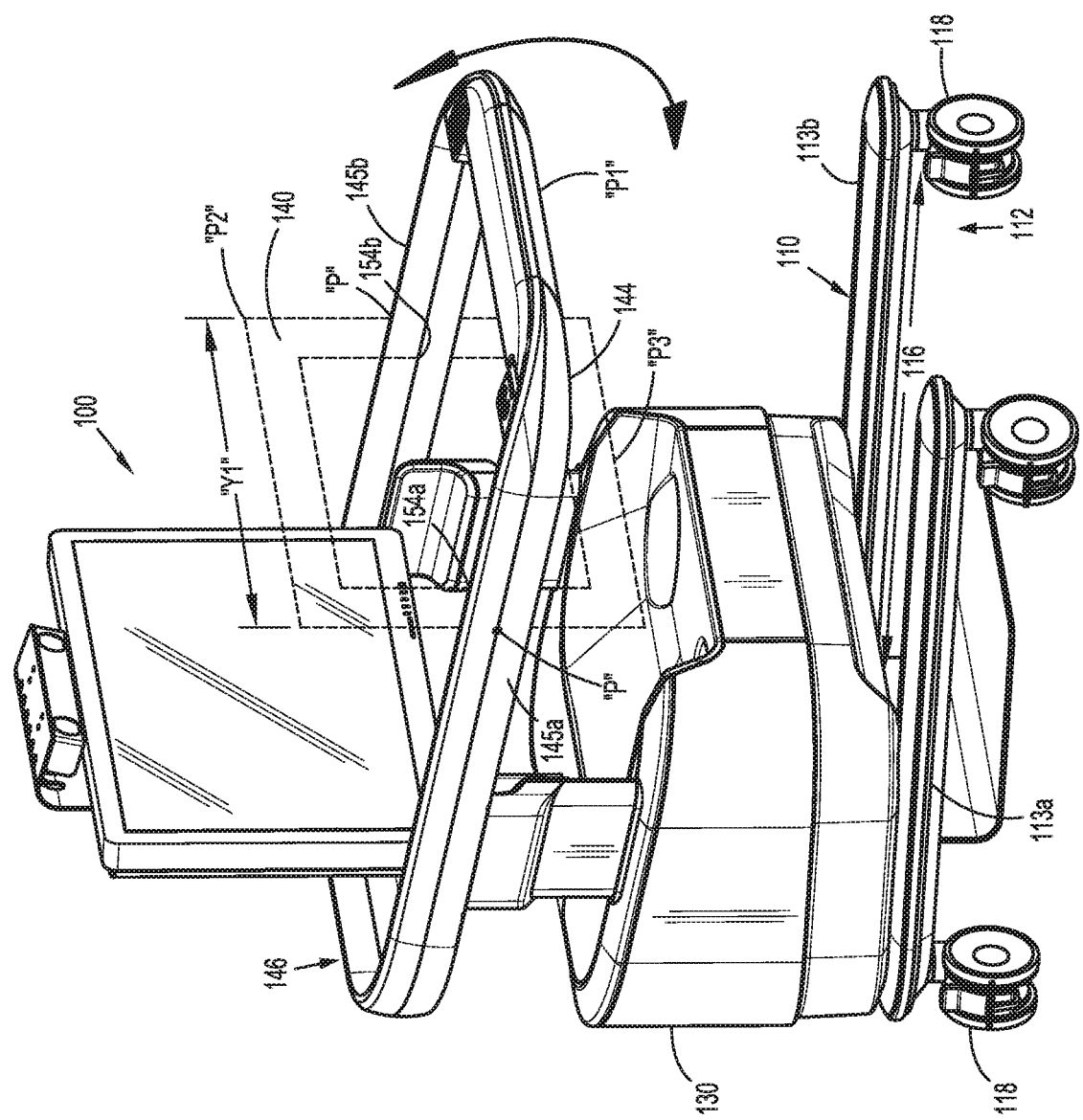
FIG. 6 is a perspective view of a mobile surgical control console, according to another embodiment of the present disclosure, illustrating a mobile section thereof pivoting from a first position to a second position.

FIG. 6 illustrates another embodiment of the present disclosure. In this embodiment, mobile section 150 is pivotable about a pivoting point or axis "P." The mobile section 150 may be connected to the upper frame assembly 140 via hinge members 154*a*, 154*b*. Hinge members 154*a*, 154*b* may allow pivoting/rotational movement ranging, in embodiments from about 0 degrees to about 180 degrees, in other embodiments from about 45 degrees to about 135 degrees, in yet other embodiments from about 75 degrees to about 95 degrees, of mobile section 150.

In use, a clinician may pivot the mobile section 150 from a first position "P1" to a second position "P2," from the first position "P1" to a third position "P3" or from the second position "P2" to the third position "P3." The clinician may pivot the mobile section 150 by exerting upward force or downward force upon the mobile section 150 (e.g., range of pivoting motion illustrated by arrow). When mobile section 150 is placed in first position "P1," mobile section 150 is aligned with the upper frame 142; whereas, when mobile section 150 is placed in either second position "P2" or third position "P3", the mobile section 150 is positioned perpendicular to the upper frame 142. In second position "P2," the mobile section 150 is placed perpendicularly above the upper frame 142, and in third position "P3," the mobile section is placed perpendicularly below the upper frame 142. Once the clinician has pivoted the mobile section 150 to the desired position, the hinge members 154*a*, 154*b* may be locked into the selected position by a locking mechanism (not explicitly shown).

After hinge members 154*a*, 154*b* are locked in the selected position, the upper frame assembly 140 is reconfigured. The upper frame assembly 140 resembles an "L" shape with mobile section 150 positioned perpendicularly to the beams 145*a*, 145*b* of the upper frame 142. By decreasing a length of the beams 145*a*, 145*b* of upper frame 142 by length "Y1," the proximal end 144 of the upper frame 142 approximately terminates prior to opening 116 defined through the proximal end 112 of the lower frame assembly 110, so that the proximal end 144 of the upper frame 142 axially aligns with the opening 116 defined through the proximal end 112 of lower frame assembly 110.

Figure 7:
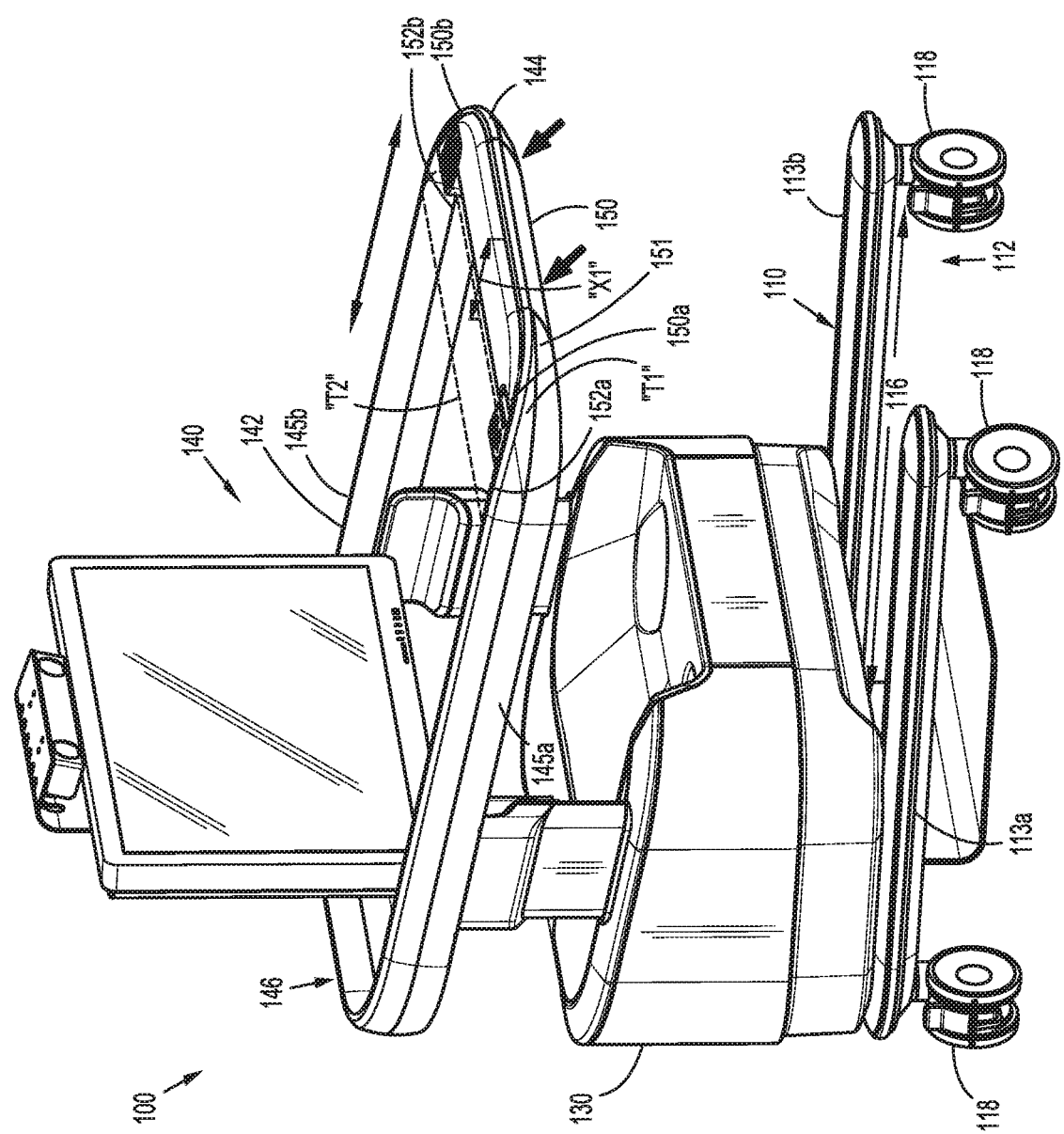
FIG. 7 is a perspective view of a mobile surgical control console, according to yet another embodiment of the present disclosure, illustrating a mobile section thereof translating from a first position to a second position.

Turning now to FIG. 7, yet another embodiment of mobile surgical control console 100, according to the present disclosure, is described. As illustrated in FIG. 7, the beams 145*a*, 145*b* of the upper frame 142 includes track portions 152*a*, 152*b*, respectively. Track portions 152*a*, 152*b* may be located upon a superior surface, an interior surface or an inferior surface of the beams 145*a*, 145*b* of the upper frame 142. The mobile section 150 includes a first end 150*a* and a second end 150*b*. The first end 150*a* and the second end 150*b* are configured to fit within track portions 152*a*, 152*b*, respectively. Mobile section 150 may translate from a first position "T1" to a second position "T2."

In use, a clinician may translate mobile section 150 by pushing and/or pulling upon the mobile section 150 (e.g., the pushing and/or pulling motion illustrated by arrows). By transitioning mobile section 150 from first position "T1" to second position "T2," the proximal end 144 of the upper frame 142 is positioned farther distally by a length "X1" creating an aperture or opening 151 within the upper frame assembly 140. This aperture or opening 151 is axially aligned with or in registration with the opening 116 defined through the proximal end 112 of the lower frame assembly 110.

Figure 8:
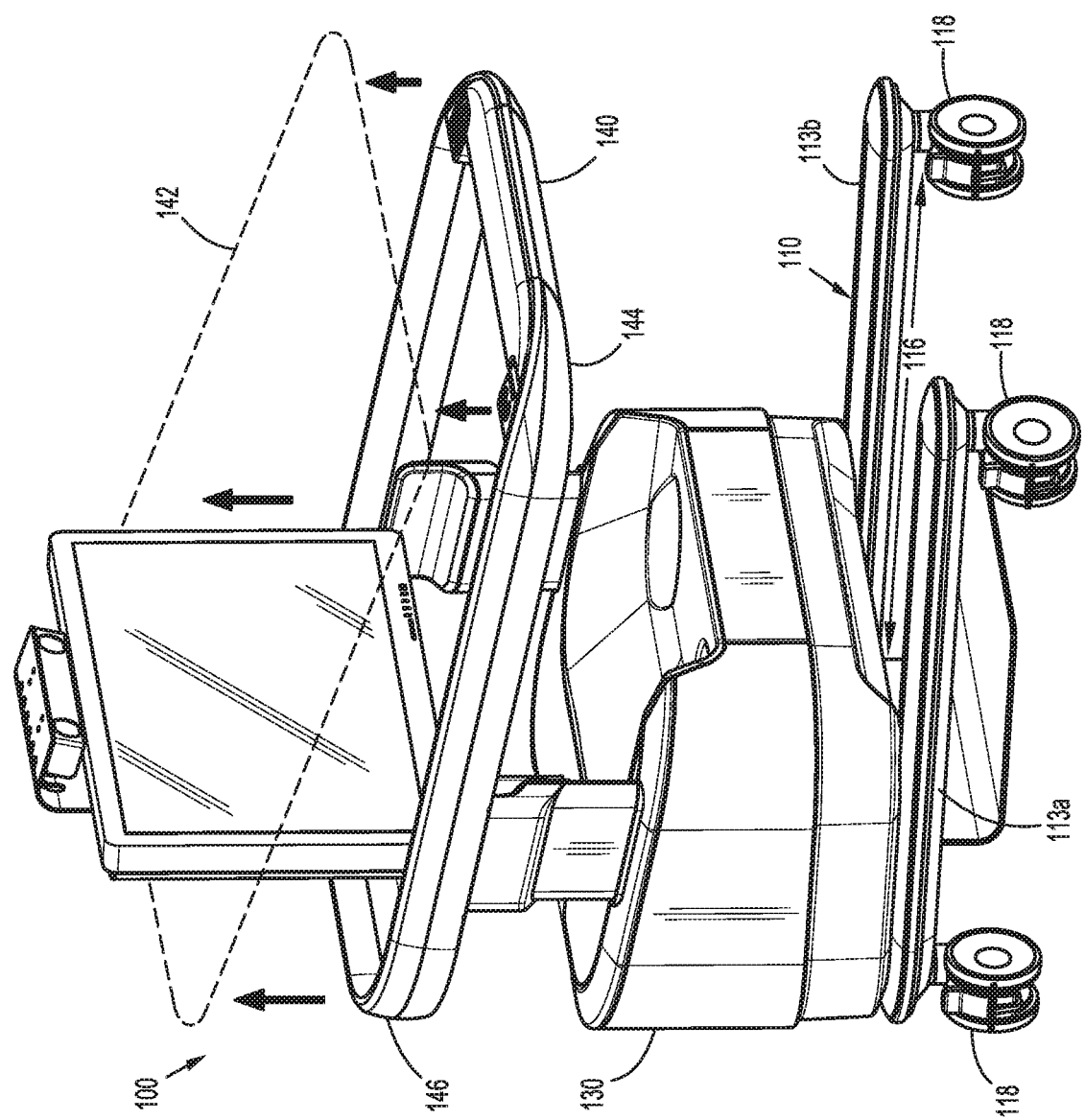
FIG. 8 is a perspective view of a mobile surgical control console, according to another embodiment of the present disclosure, illustrating an upper frame thereof transitioning between a first position and a second position.
Figure 9:
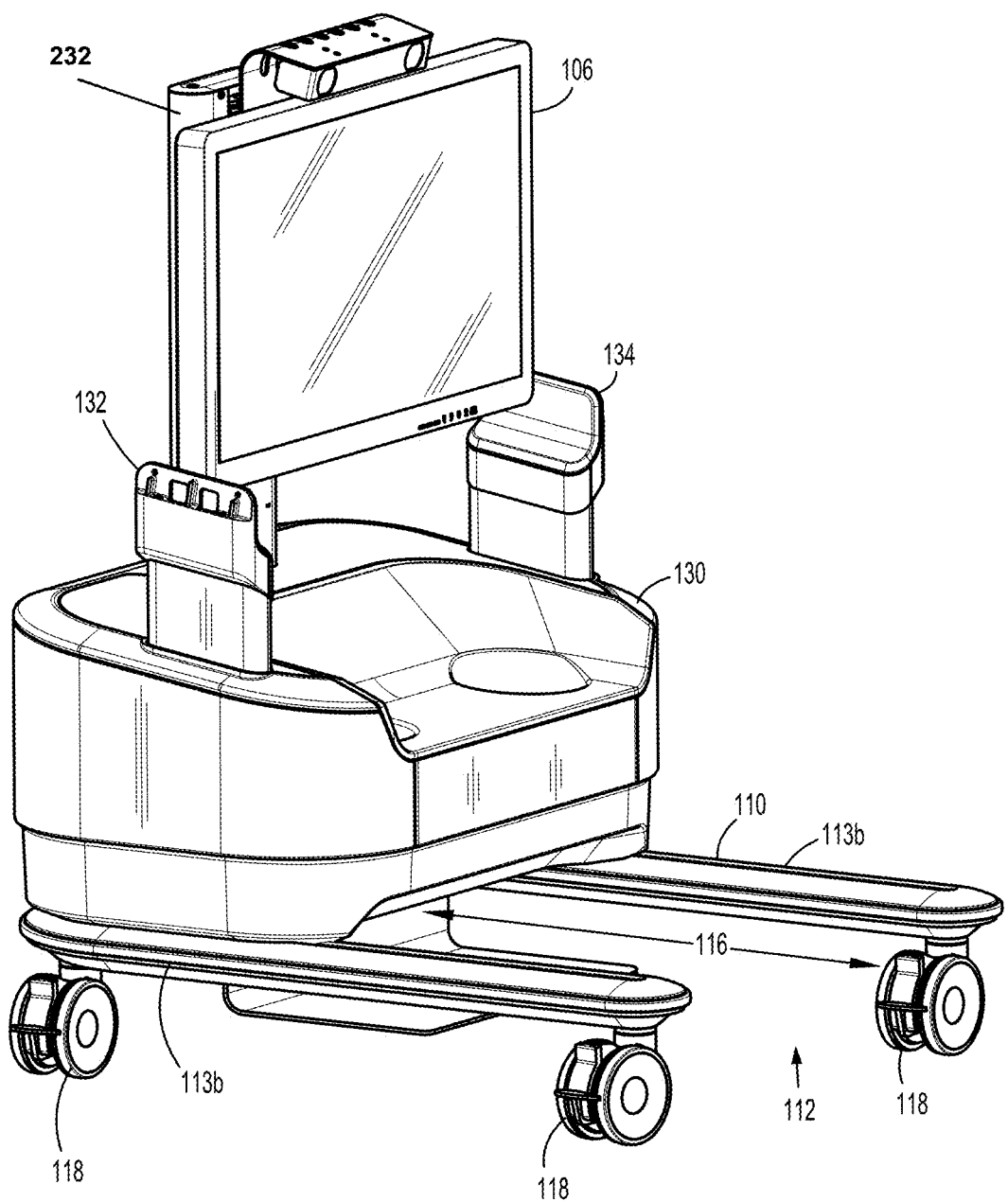
FIG. 9 is a perspective view of the mobile surgical control console of FIG. 8.

Referring now to FIGS. 8 and 9, in accordance with another embodiment of the present disclosure, the upper frame 142 is removable from the mobile surgical control console 100. In one embodiment, the upper frame 142 is removably connected to vertical supports 132, 134 allowing the upper frame 142 to be completely detached from the mobile surgical control console 100. In this embodiment, the upper frame 142 may be connected to the vertical supports 132, 134 via a snap-fitting, which allows a clinician to snap the upper frame 142 in and out of the mobile surgical console 100 without the need of any tools or the like. A clinician may detach the upper frame 142 by exerting upward force upon the upper frame 142 (e.g., upward force illustrated by arrows).

As illustrated in FIGS. 10-13, in accordance with yet another embodiment of the present disclosure, the upper frame 142 is pivotably connected to the mobile surgical control console 100. In one embodiment, the upper frame 142 is pivotably connected to the vertical supports 132, 134 via pivoting members 158*a*, 158*b*, respectively. In this embodiment, the upper frame 142 may pivot between a first position "U1" and a second position "U2." Once the upper frame 142 is pivoted to the second position "U2," the upper frame 142 may be locked in the second position "U2" by locking mechanisms 156*a*, 156*b*. Accordingly, the dimensions of the mobile surgical control console 100 are changed once the upper frame 142 is locked into the second position "U2."

Figure 10:
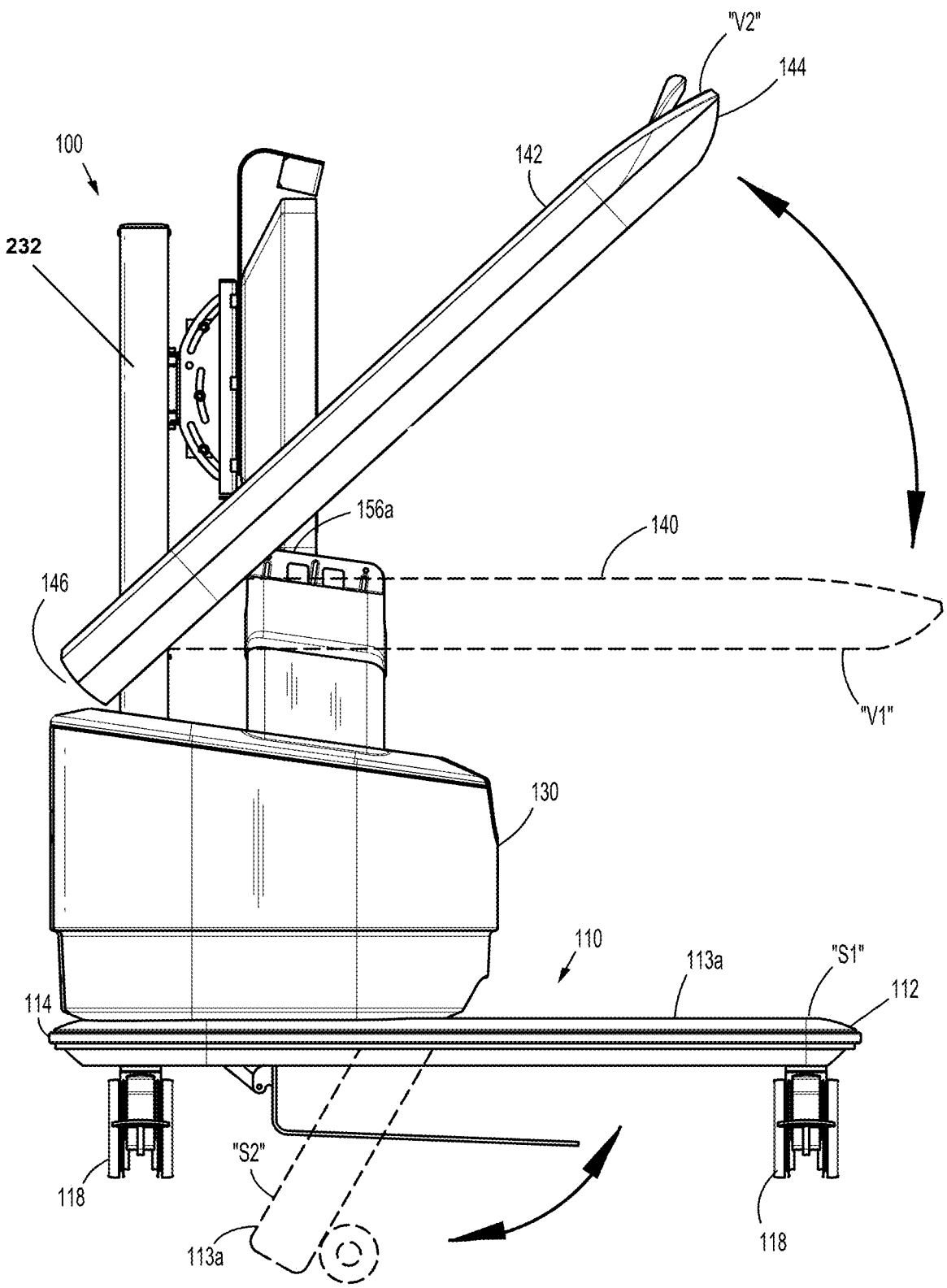
FIG. 10 is a side view of a mobile surgical control console, according to an additional embodiment of the present disclosure, illustrating an upper frame thereof pivoting between a first position and a second position, and illustrating a lower frame thereof swinging between a first position and a second position.
Figure 11:
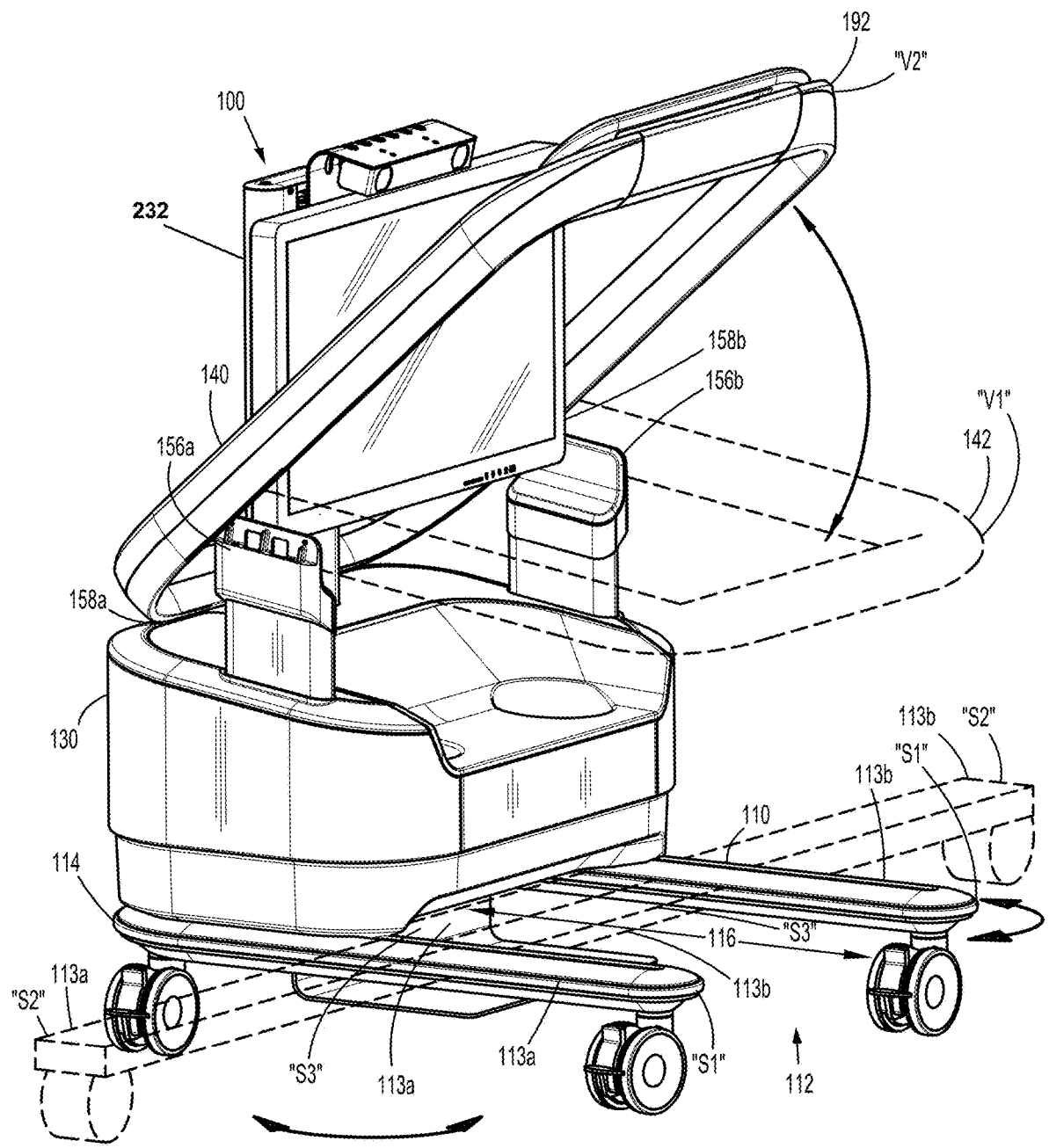
FIG. 11 is a perspective view of the mobile surgical control console of FIG. 10.

With reference now to FIGS. 10 and 11, as briefly discussed above, in some embodiments each beam 113*a*, 113*b* of the lower frame assembly 110 may optionally include a hinged section 120*a*, 120*b*, respectively, that allows a swinging motion of each beam 113*a*, 113*b*. Each beam 113*a*, 113*b* of the lower frame assembly 110 may swing from a first position "S1" to a second position "S2", from the first position "S1" to a third position "S3" or from the second position "S2" to the third position "S3." Once each beam 113*a*, 113*b* is transitioned to the selected position, each beam 113*a*, 113*b* may be locked into the selected position with locking mechanism 122*a*, 122*b*, respectively.

In use, a clinician may choose to transition only one of beams 113*a*, 113*b* or may choose to transition both beams 113*a*, 113*b*. In embodiments, a clinician may choose to transition both beams 113*a*, 113*b* from first position "S1" to either second or third position "S2" or "S3," whereby the mobile surgical control console 100 is reconfigured, so that the transitioning length of each beam 113*a*, 113*b* is displaced to either second or third position "S2" or "S3."

Figure 12:
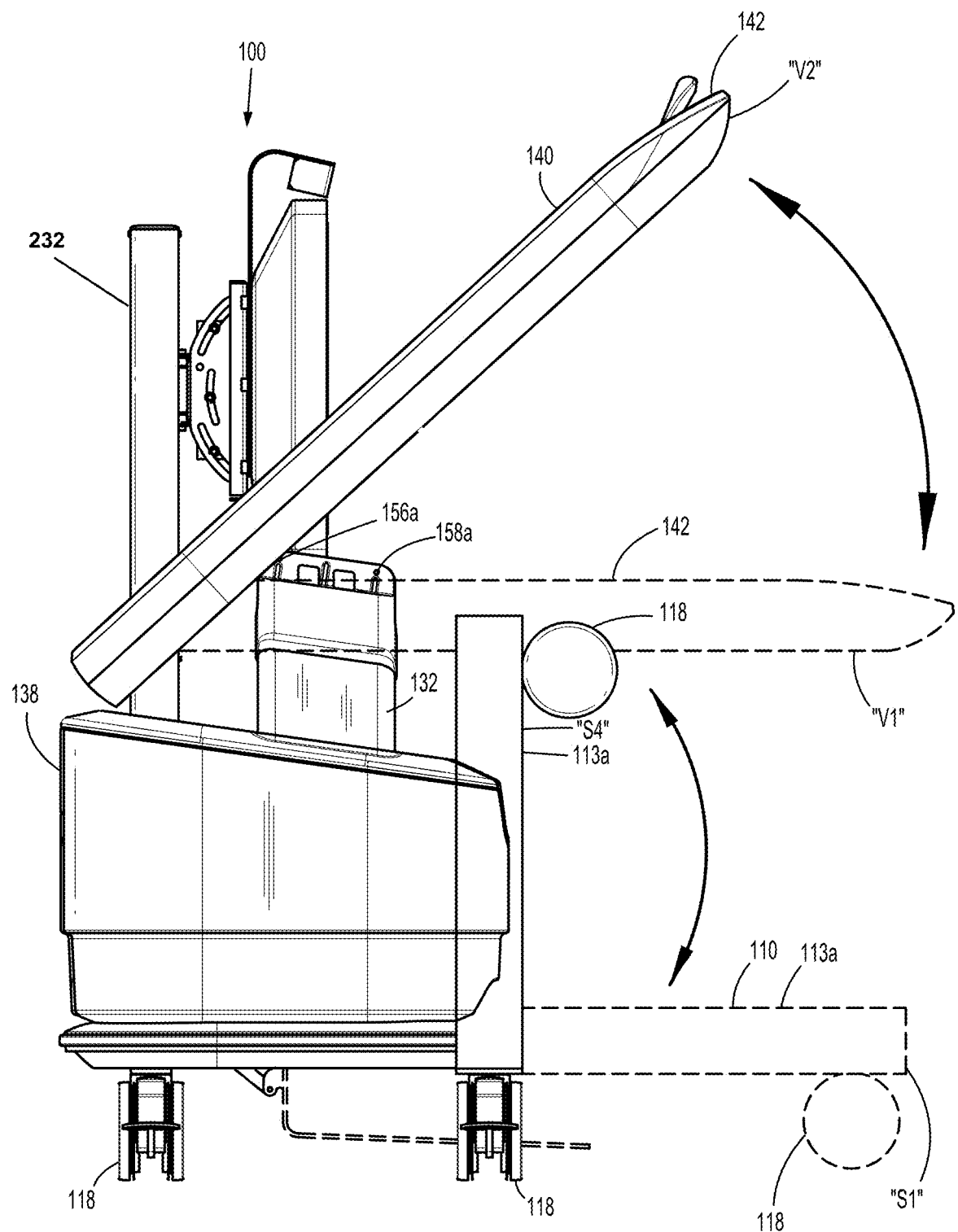
FIG. 12 is a side view of a mobile surgical control console, according to yet another embodiment of the present disclosure illustrating, an upper frame pivoting between a first position and a second position, and illustrating a lower frame thereof pivoting between a first position and a second position.
Figure 13:
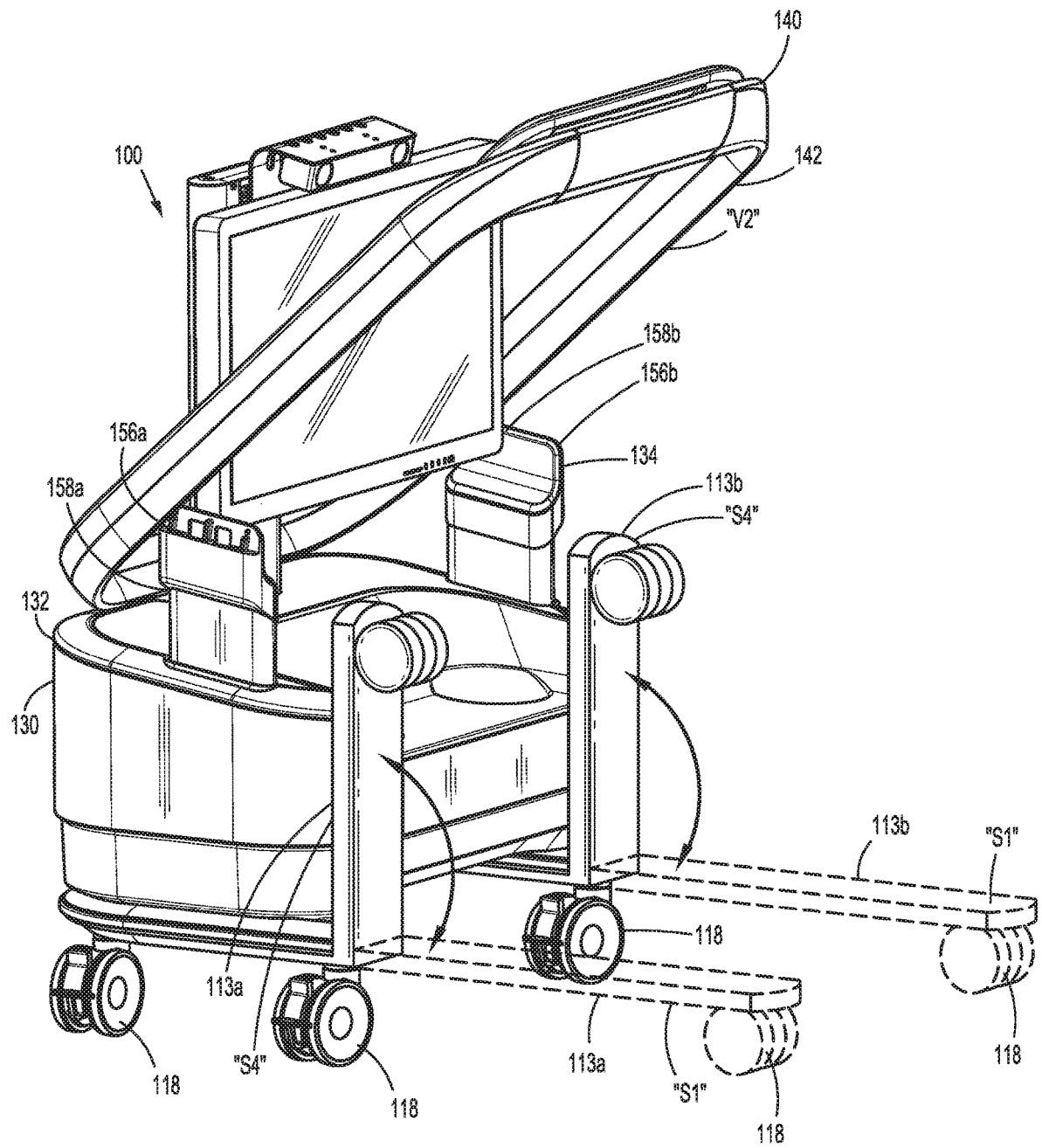
FIG. 13 is a side view of the mobile surgical control console of FIG. 12.

With reference now to FIGS. 12 and 13, in other embodiments each beam 113*a*, 113*b* of the lower frame assembly 110 may optionally include a hinged section 120*a*, 120*b*, respectively, that allows a pivoting motion. Each beam 113*a*, 113*b* of the lower frame assembly 110 may pivot from a first position "S1" to a fourth position "S4." When beams 113*a*, 113*b* are placed in fourth position "P4," each beam 113*a*, 113*b* resembles an "L" shape, with the transitioning length of each beam 113*a*, 113*b* positioned perpendicularly to the non-transitioning length of each beam 113*a*, 113*b*. Once each beam 113*a*, 113*b* is pivoted to the selected position, each beam 113*a*, 113*b* may be locked into the selected position with locking mechanism 122*a*, 122*b*, respectively.

In use, a clinician may choose to pivot only one of beams 113*a*, 113*b* or may choose to transition both beams 113*a*, 113*b*. In embodiments that a clinician chooses to pivot both beams 113*a*, 113*b* from the first position "S1" to the fourth position "S4," the mobile surgical control console 100 will be reconfigured. The pivoting length of each beam 113*a*, 113*b* will be positioned perpendicularly to the non-pivoting length of each beam 113*a*, 113*b* reducing the horizontal length of each beam 113*a*, 113*b*.

Figure 14:
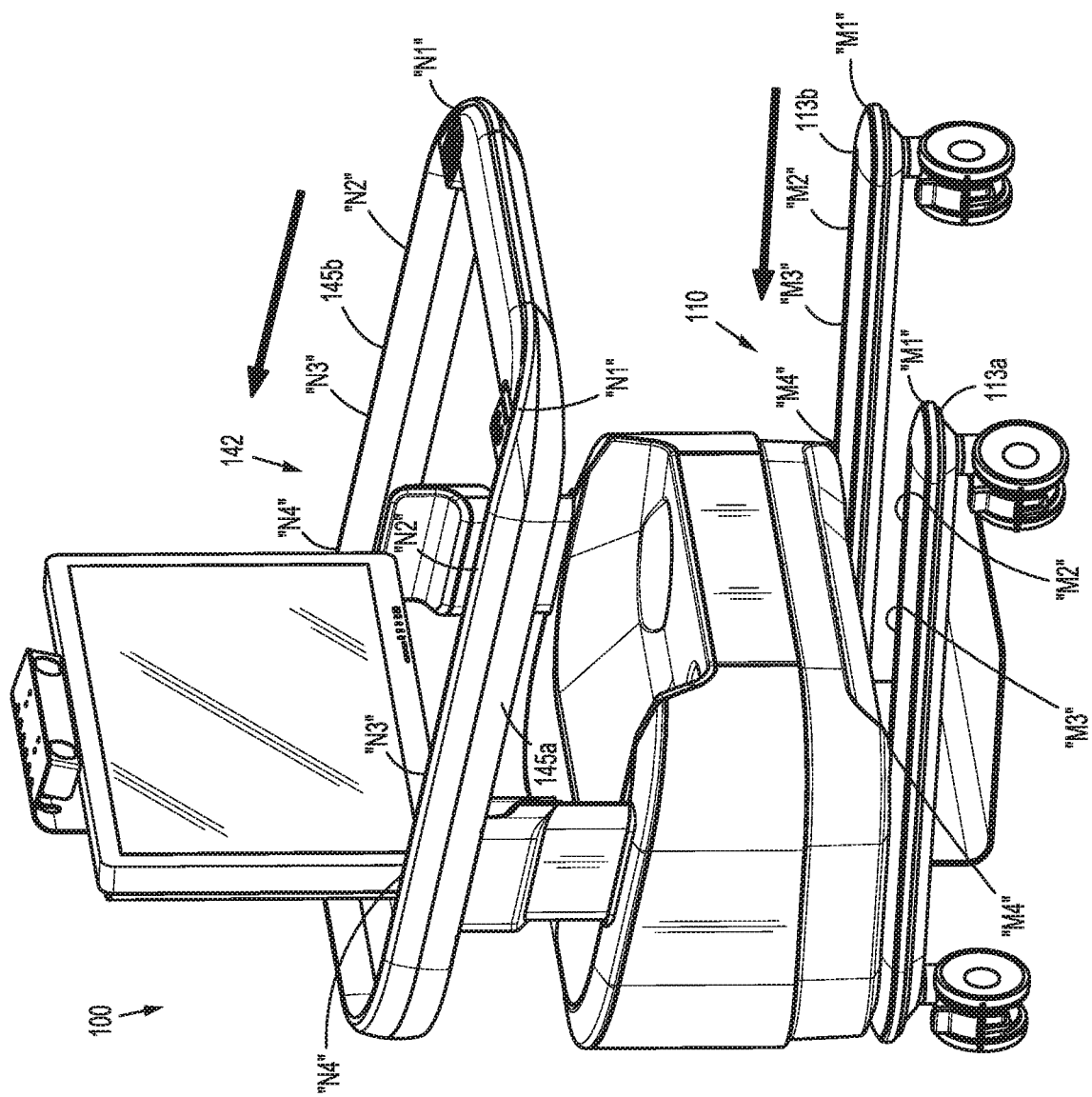
FIG. 14 is a side view of a mobile surgical control console, according to yet another embodiment of the present disclosure illustrating, an upper frame thereof transitioning between a first position, a second position, a third position and a fourth position, and illustrating a lower frame assembly thereof transitioning between the first, second, third and fourth positions.

Moving to FIG. 14, according to another embodiment of surgical control console 100, each beam 113*a*, 113*b* of the lower frame assembly 110 and each beam 145*a*, 145*b* of the upper frame 142 may optionally include a telescoping mechanism that allows extension/retraction of each beam 113a, 113b and 145a, 145b. Each beam 113a, 113b may transition from a first position "M1" (first length) to a second position "M2" (second length shorter than the first length), or a third position "M3" (third length shorter than the second length) or a fourth position "M4" (fourth length shorter than the third length). Transitioning each beam 113a, 113b from the first position "M1" to any of the other denoted positions will shorten the length of each beam 113a, 113b, whereas when each beam 113a, 113b is transitioned to the fourth position "M4" each beam 113a, 113b is at its shortest length. The location of positions "M2", "M3", and "M4" of beams 113a, 113b may be fixed or may be fluid, meaning the clinician can adjust the location of each position based on the clinician's needs.

The telescoping mechanism included in each beam 145a, 145b works similar to the telescoping mechanism in each beam 113a, 113b. Each beam 145a, 145b may be transitioned from a first position "N1" (first length) to a second position "N2" (second length shorter than the first length) or a third position "N3" (third length shorter than the second length) or a fourth position "N4" (fourth length shorter than the third length). Also, transitioning each beam 145a, 145b from the first position "N1" to any of the other denoted positions will shorten the length of each beam 145a, 145b with the fourth position "N4" being the shortest position for each beam 145a, 145b. The location of positions "N2", "N3", and "N4" of beams 145a, 145b may also be fixed or fluid.

Figure 15:
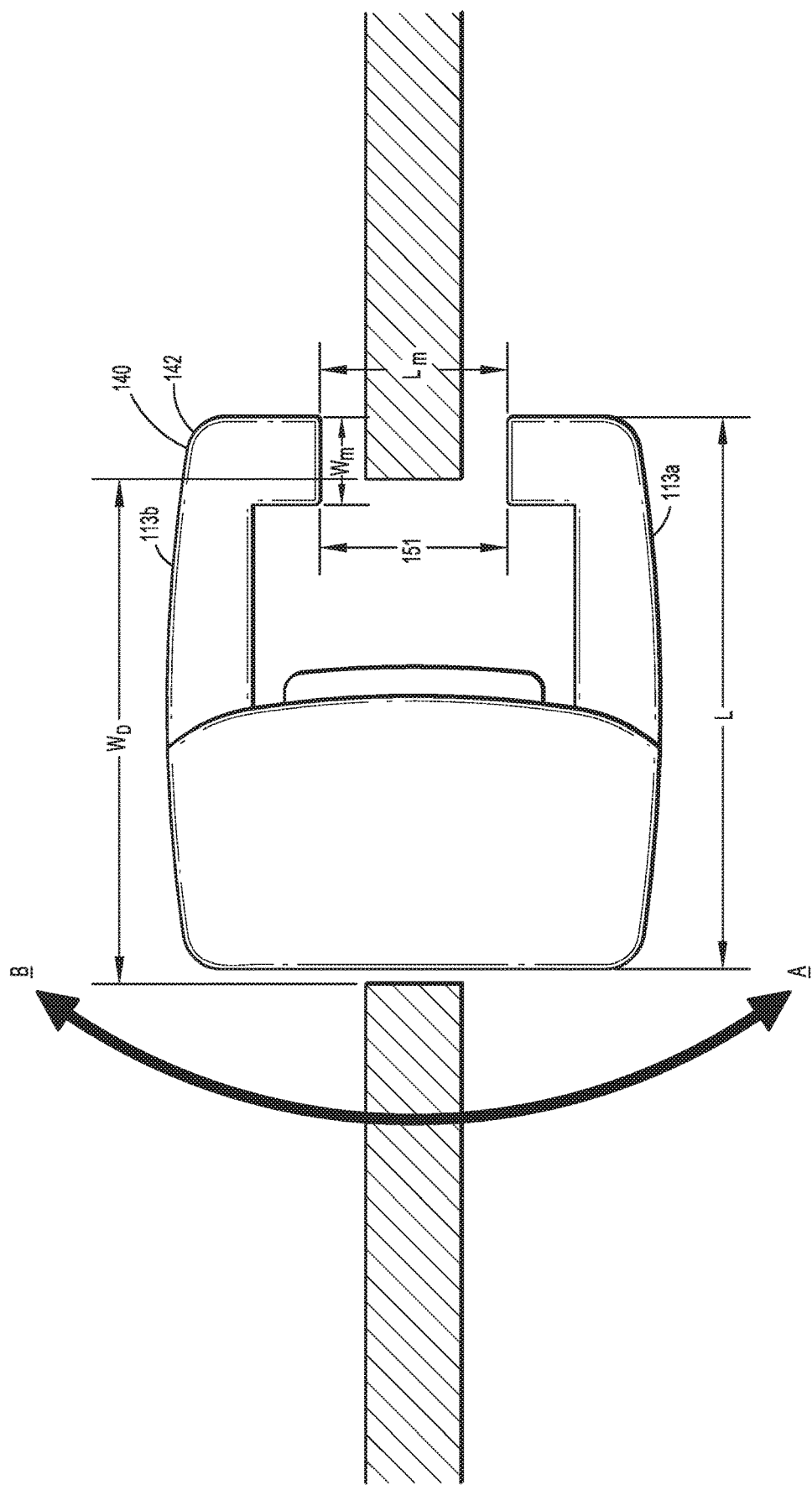
FIG. 15 is a top plan view of a mobile surgical control console, in accordance with the principles of the present disclosure, transitioning between location A and location B.

Turning now to FIG. 15, a method of moving mobile surgical control console 100, across a fixed dimensioned opening of a threshold, will be described in accordance with the present disclosure. In use, a clinician may reconfigure mobile surgical control console 100 by removing mobile section 150 from the upper frame 142 (See FIGS. 3-5), pivoting mobile section 150 from first position "P1" to second position "P2" (See FIG. 6), or translating mobile section 150 from first position "T1" to second position "T2" (see FIG. 7). After the mobile section 150 is either removed, pivoted or transitioned to selected position, the upper frame assembly 140 will include an opening 151 which is aligned with the opening 116 defined through the proximal end 112 of the lower frame assembly 110. Prior to the displacement of mobile section 150, the mobile surgical control console 100 has a first dimension where the width of the mobile surgical console 100 is greater than about 30 inches and the length of the mobile surgical console 100 is also greater than about 30 inches.

After being so reconfigured, the mobile surgical control console 100 may then be moved across a threshold from a first location "A" to a second location "B" by pivoting the mobile surgical control console 100 through an opening of the threshold by first receiving a portion of the threshold into the opening 116 of the lower frame assembly 110 and the opening 151 of the upper frame assembly 140.

After the displacement of mobile section 150 and the reconfiguration of mobile surgical control console 100, the mobile surgical control console 100 has a second dimension where the upper frame assembly 140 includes opening 151. At the point where opening 151 exists within the upper frame 142, the length "L" of mobile surgical control console 100 is reduced at least a width "$W_M$" of mobile section 150. The reduction in the length "L" of mobile surgical control console 100 by width "$W_M$" of mobile section 150 allows mobile surgical control console 100 to pass through a threshold with a width "$W_D$" (e.g., approximately 33 inches).

Opening 151 of the upper frame 142 has appropriate dimension to allow a standard threshold to fit within the opening 151 of the upper frame (e.g., the length being "$W_L$" and the width "$W_M$"). The width "$W_M$" of mobile section 150 ranges in embodiments from about 1 inch to about 7 inches, in other embodiments from about 2 inches to about 5 inches, in yet other embodiments from about 3 inches to about 4 inches. The length of mobile section 150 ranges in embodiments from about 1 inch to about 20 inches, in other embodiments from about 3 inches to about 18 inches, in yet other embodiments from about 6 inches to about 16 inches.

A second method of moving mobile surgical control console 100 will be described in accordance with the present disclosure. In use, a clinician will select between pivoting beams 113a, 113b from first position "S1" to fourth position "S4" or swinging beams 113a, 113b from first position "S1" to either second position "S2" or third position "S3." After beams 113a, 113b are positioned in selected position, a clinician will select between removing mobile section 150 from the upper frame 142, pivoting mobile section 150 from first position "P1" to second position "P2" or translating mobile section 150 from first position "T1" to second position "T2." Prior to the repositioning of beams 113a, 113b and the displacement of mobile section 150, the mobile surgical control console 100 has a first dimension where the width of mobile surgical console 100 is greater than about 30 inches and the length of the mobile surgical console 100 is greater than about 30 inches.

After the mobile section 150 is either removed, pivoted or transitioned to selected position, the upper frame assembly 140 will include an opening 151. The mobile surgical control console 100 will be moved across a threshold from a first location "A" to a second location "B" by pivoting the mobile surgical control console 100 through the threshold by first receiving a portion of the threshold into the opening 151 of the upper frame assembly 140.

After the repositioning of beams 113a, 113b and the displacement of mobile section 150, the mobile surgical control console 100 has a second dimension where the lower frame assembly 110 is reduced by a length of each beam 113a, 113b and the upper frame 142 includes opening 151. The length of each beam 113a, 113b that is repositioned ranges in embodiments from about 1 inch to about 26 inches, in other embodiments from about 5 inches to about 22 inches, in yet other embodiments from about 10 inches to about 20 inches.

At the point where opening 151 exist within the upper frame 142, the mobile surgical control console 100 length is reduced by the width "$W_m$" of mobile section 150. The width of mobile section 150 ranges in embodiments from about 1 inch to about 7 inches, in other embodiments from about 2 inches to about 5 inches, in yet other embodiments from about 3 inches to about 4 inches.

Another method of moving mobile surgical control console 100 will be described in accordance with the present disclosure. In use, a clinician will select between pivoting beams 113a, 113b from first position "S1" to forth position "S4," swinging beams 113a, 113b from first position "S1" to either second position "S2" or third position "S3" or keeping beams 113a, 113b in first position "S1." Prior to the repositioning of beams 113a, 113b and the displacement of upper frame 142, the mobile surgical control console 100 has a first dimension where the width of mobile surgical console 100 is greater than about 34 inches and the length of the mobile surgical control console 100 is greater than about 44 inches.

After beams 113a, 113b are positioned in selected position, the clinician will select between removing upper frame 142 or pivoting upper frame 142 from first position "U1" to second position "U2." The mobile surgical control console 100 will be moved across a threshold from a first location "A" to a second location "B" by pushing the mobile surgical control console 100 through the threshold or by pivoting the mobile surgical control console 100 through the threshold by first receiving a portion of the threshold in to the opening 116 of the lower frame assembly 110.

In embodiments where the beams 113a, 113b are repositioned from first position "S1" and the upper frame 142 is displaced, the mobile surgical control console 100 has a second dimension where the lower frame assembly is reduced by a length of each beam 113a, 113b and the mobile surgical control console 100 is reduced by a length of the upper frame 142. The length of each beam 113a, 113b that is repositioned ranges in embodiments from about 1 inch to about 26 inches, in other embodiments from about 5 inches to about 22 inches, in yet other embodiments from about 10 inches to about 20 inches. The length of the upper frame 142 that is displaced ranges in embodiments from about 1 inch to about 22 inches, in other embodiments from about 5 inches to about 18 inches, in yet other embodiments from about 10 inches to about 16 inches.

In other embodiments where the beams 113a, 113b are not repositioned from first position "S1" and the upper frame assembly 140 is displaced, the mobile surgical control console 100 has a third dimension where the mobile surgical control console 100 is reduced by a length of the upper frame 142. The length of the upper frame 142 that is displaced ranges in embodiments from about 1 inch to about 24 inches, in other embodiments from about 5 inches to about 20 inches, in yet other embodiments from about 10 inches to about 18 inches.

It will be understood that various modifications may be made to the embodiments of the presently disclosed mobile surgical consoles. Therefore, the above description should not be construed as limiting, but merely as exemplification of embodiments. Those skilled in the art will envision other modifications within the scope and spirit of the present disclosure.

What is claimed is:

1. A mobile surgical control console, comprising:
   a base housing;
   a lower frame assembly coupled to the base housing, the lower frame assembly including a proximal end, a distal end and an opening defined therethrough and which opening extends through the distal end of the lower frame assembly, the lower frame assembly including:
      a first leg located along a first side of the control console and extending between the proximal end and the distal end of the lower frame assembly; and
      a second leg located along a second side of the control console, opposite the first side, and extending between the proximal end and the distal end of the lower frame assembly;
   a plurality of wheels attached to the first leg and the second leg of the lower frame assembly and supporting the lower frame assembly thereon;
   a plurality of vertical supports attached to the base housing, the plurality of vertical supports including a first support extending from the first leg, and a second support extending from the second leg, each vertical support having an inferior end and a superior end;
   a monitor attached to a superior end of a monitor vertical support; and
   an upper frame assembly supported on the plurality of vertical supports, the upper frame assembly including:
      an upper frame including a proximal end, a distal end and an opening defined therethrough and which opening extends through the distal end of the upper frame assembly, the upper frame assembly including:
         a first arm located along the first side of the control console and extending between the proximal end and the distal end of the upper frame assembly, wherein the first arm is in vertical registration with and is spaced a vertical distance from the first leg; and
         a second arm located along the second side of the control console and extending between the proximal end and the distal end of the upper frame assembly, wherein the second arm is in vertical registration with and is spaced a vertical distance from the second leg; and
      a mobile section supported by the upper frame and extending between and interconnecting the first arm and the second arm.

2. The mobile surgical control console according to claim 1, wherein the mobile section is configured to be detached from the upper frame.

3. The mobile surgical control console according to claim 1, wherein the lower frame assembly is substantially U-shaped.

4. The mobile surgical control console according to claim 1, wherein the opening in the lower frame assembly is axially aligned with the mobile section of the upper frame assembly.

5. A mobile surgical control console, comprising:
   a base housing;
   a lower frame assembly coupled to the base housing, the lower frame assembly including a proximal end, a distal end and an opening defined therethrough and which opening extends through the distal end of the lower frame assembly, the lower frame assembly including:
      a first leg located along a first side of the control console and extending between the proximal end and the distal end of the lower frame assembly; and
      a second leg located along a second side of the control console, opposite the first side, and extending between the proximal end and the distal end of the lower frame assembly;
   a plurality of wheels attached to the first leg and the second leg of the lower frame assembly and supporting the lower frame assembly thereon;
   a plurality of vertical supports attached to the base housing, the plurality of vertical supports including a first support extending from the first leg, and a second support extending from the second leg, each vertical support having an inferior end and a superior end;
   a monitor attached to a superior end of a monitor vertical support; and
   an upper frame assembly supported on the plurality of vertical supports, the upper frame assembly including:
      an upper frame including a proximal end, a distal end and an opening defined therethrough and which opening extends through the distal end of the upper frame assembly, the upper frame assembly including:
         a first arm located along the first side of the control console and extending between the proximal end and the distal end of the upper frame assembly, wherein the first arm is in vertical registration with and is spaced a vertical distance from the first leg; and a second arm located along the second side of the control console and extending between the proximal end and the distal end of the upper frame assembly, wherein the second arm is in vertical registration with and is spaced a vertical distance from the second leg.

6. A mobile surgical control console, comprising:

a lower frame assembly including a proximal end, a distal end and a lower opening defined therethrough, wherein the lower opening extends through the distal end of the lower frame assembly, the lower frame assembly including:

a first leg located along a first side of the control console and extending between the proximal end and the distal end of the lower frame assembly; and a second leg located along a second side of the control console, opposite the first side, and extending between the proximal end and the distal end of the lower frame assembly, and wherein the lower opening is located between the first leg and the second leg;

a plurality of wheels including a first pair of wheels supporting the first leg and a second pair of wheels supporting the second leg;

a plurality of vertical supports connected to the lower frame assembly, the plurality of vertical supports including a first support extending from the first leg, and a second support extending from the second leg;

a monitor supported on a monitor vertical support;

an upper frame assembly supported on the plurality of vertical supports and being spaced a vertical distance from the lower frame assembly, the upper frame assembly including a proximal end, a distal end and an upper opening defined therethrough, wherein the upper opening extends through the distal end of the upper frame assembly, the upper frame assembly including:

a first arm located along the first side of the control console and extending between the proximal end and the distal end of the upper frame assembly, wherein the first arm is in vertical registration with the first leg; and a second arm located along the second side of the control console and extending between the proximal end and the distal end of the upper frame assembly, wherein the second arm is in vertical registration with the second leg, and wherein and the upper lower opening is located between the first arm and the second arm; and a mobile section supported by and interconnecting the first arm and the second arm of the upper frame assembly.

7. The mobile surgical control console according to claim 6, wherein the mobile section is configured to be detached from the upper frame.

8. The mobile surgical control console according to claim 6, wherein the lower frame assembly is substantially U-shaped.

9. The mobile surgical control console according to claim 6, wherein the lower opening in the lower frame assembly is vertically axially aligned with the mobile section of the upper frame assembly.

* * * * *